(12) United States Patent
Malone

(10) Patent No.: US 7,904,309 B2
(45) Date of Patent: Mar. 8, 2011

(54) ASSESSING AND MANAGING WORK-RELATED MUSCULOSKELETAL INJURIES

(76) Inventor: K. Scott Malone, Warner Robins, GA (US)

( * ) Notice: Subject to any disclaimer, the term of this patent is extended or adjusted under 35 U.S.C. 154(b) by 1300 days.

(21) Appl. No.: 11/454,731

(22) Filed: Jun. 16, 2006

(65) Prior Publication Data

US 2006/0287879 A1    Dec. 21, 2006

Related U.S. Application Data

(60) Provisional application No. 60/691,062, filed on Jun. 16, 2005.

(51) Int. Cl.
   *G06Q 10/00* (2006.01)
(52) U.S. Cl. .................................. 705/2; 705/3
(58) Field of Classification Search .................. 128/898; 705/2; 702/19; 482/8
   See application file for complete search history.

(56) References Cited

U.S. PATENT DOCUMENTS

| | | | | |
|---|---|---|---|---|
| 5,848,594 | A  * | 12/1998 | Matheson | 128/898 |
| 6,821,257 | B1 * | 11/2004 | Jolley | 600/595 |
| 6,865,581 | B1 * | 3/2005 | Cloninger et al. | 1/1 |
| 2002/0138306 | A1 * | 9/2002 | Sabovich | 705/3 |
| 2003/0105648 | A1 * | 6/2003 | Schurenberg et al. | 705/2 |
| 2004/0006432 | A1 * | 1/2004 | Lau et al. | 702/19 |
| 2006/0252600 | A1 * | 11/2006 | Grogan et al. | 482/8 |

* cited by examiner

*Primary Examiner* — Gerald J. O'Connor
*Assistant Examiner* — Teresa Woods
(74) *Attorney, Agent, or Firm* — Merchant & Gould

(57) ABSTRACT

Methods, systems, and computer program products assess and manage work-related musculoskeletal injuries associated with one or more work sites. A method involves defining musculoskeletal injury categories and drawing relationships between the musculoskeletal injury categories by applying specialized medical knowledge. The relationships prevent informational disconnect between slightly disparate diagnoses between physicians who evaluate a same patient for the work-related musculoskeletal injury. The method also involves structuring storage of the relationships in a relational database, gathering for each work site, demographics and statistics on work-related musculoskeletal injuries associated with at least one of relatively high lost time or relatively high medical cost, and utilizing the relationships and the demographics to compile and retrieve data that facilitates prevention or improved resolution of the musculoskeletal injury.

18 Claims, 4 Drawing Sheets

ASSESSING AND MANAGING WORK-RELATED MUSCULOSKELETAL INJURIES

RELATED APPLICATIONS

This utility patent application claims the benefit under 35 United States Code §119(e) of U.S. Provisional Patent Application No. 60/691,062 filed on Jun. 16, 2005, which is hereby incorporated by reference.

COPYRIGHT NOTICE

A portion of the disclosure of this patent document contains material, which is subject to copyright protection. The copyright owner has no objection to the facsimile reproduction by anyone of the patent document or patent disclosure as it appears in the U.S. Patent and Trademark Office patent file or records, but otherwise reserves all copyright rights whatsoever.

TECHNICAL FIELD

This invention relates to methods of assessing and managing work-related musculoskeletal injuries.

BACKGROUND

A variety of problems exist with conventional methods of assessing and managing job or work-related musculoskeletal injuries in the Federal Government DOD (Department of Defense. The DOD process of assessing and managing work-related injuries is based on a model developed in the 1960's. Multiple federal agencies, such as injury compensation, occupational medical service (OMS), defense commissary association (DeCA), defense logistics agency (DLA), and defense reutilization and marketing service (DRMS), can have different regulations for accepting and managing work-related injuries. Also, poor communication between injured workers, employers, authorizing agencies and physicians can add increased costs and delays to the compensation and recovery periods. Each involved party has a different perspective on the injury assessment and management process. Injured employees may view the process with suspicion and uncertainty concerning their physical and financial future. They are concerned that they may not get the best care or they are fearful that if they return to work they will be injured worse.

Further, relatively few private physicians understand the federal DOD injury assessment and management processes. They become unhappy with the bureaucracy, paper work, and authorization processes that require extra federally trained staff. Also, statistics show that medical school graduates are weak in musculoskeletal knowledge. 1998 statistics reported that although roughly 25% of visits to primary care physicians are for musculoskeletal problems, typically less than 3% of the undergraduate medical school curriculum is spent on musculoskeletal medicine. (THE PHYSICIAN AND SPORTSMEDICINE—VOL 27—no. 3—March 98.) Statistics as recent as 2004 show that graduates still exit medical school without sufficient core knowledge in the musculoskeletal area.

Still further, employers may view injured employees with suspicion. Employers worry about the rising cost and lost time from work. They also can become skeptical about the claim and motivation of the physician and employee. The different agencies may have concerns about all parties involved. These agencies lack ongoing local training for medical providers, each agency seems to have their own set of rules that are not easy to find or interpret, and they are difficult to reach on the phone.

The musculoskeletal injury area has evidence of needing focused attention. For instance out of 11 million work-related injuries per year, the majority are sprain and strains. Back and neck injuries represent over 25% of presenting diagnoses. Physicians use a periodically updated international coding database containing international classification of diseases (ICD) for defining patient diagnoses before treatment. The ICD coding standard (currently ICD9) provides a numeric code and a brief text description of a medical problem a physician identifies in each patient. The ICD coding standard provides a vehicle for somewhat consistent application of diagnosis values. However, its organization structure is insufficient for preventing informational disconnects between even slightly disparate diagnoses between physicians who evaluate the same patient for a malady and for facilitating computational linkage between specific diagnosis values and more generalized diagnosis values.

As an example, one big problem with the current federal injury process takes into account integrated care models developed by the DOD and algorithms to justify authorizations for treatments. If the diagnosis for injury presented for payment to the DOD does not match the initial diagnosis assigned by the first treating medical provider, payment is denied and more justification is required. This process delays care from several perspectives. The employee is not authorized to receive further care, the medical provider is denied payment, the case is essentially placed on-hold, and in the worst case scenario, the employee could be responsible for the medical bill. If an employee is taken out of work, he could possibly stay out on pay while the case is on hold.

Accordingly there is an unaddressed need in the industry to address the aforementioned and other deficiencies and inadequacies.

SUMMARY

This Summary is provided to introduce a selection of concepts in a simplified form that are further described below in the Detailed Description. This Summary is not intended to identify key features or essential features of the claimed subject matter, nor is it to be used as an aid in determining the scope of the claimed subject matter.

Embodiments of the present invention include processes for assessing and managing work-related musculoskeletal injuries that shift the focus of work-related injury management to qualified local medical networks. Local comprehensive injury management teams are assembled. For instance, teams are composed of federal and private medical and administrative professionals. Injury prevention, rehabilitation, and key communication with all parties are the primary focuses. Key staff members may include physicians, nurse case managers, compensation coordinators, marketing staff, physical therapists, occupational therapists, and vocational rehabilitation specialists.

The process also includes job site analysis for occupations that have a high injury profile with regard to lost time and/or cost. Job descriptions are developed and provided to treating physicians. If the physician is not able to visit an actual job site, a video presentation is sent to the treating physician. Early intervention is implemented as soon as potential catastrophic work injuries are identified. Categories for a job-related injury are defined and agreed upon by all of the agencies involved. These agreed upon categories are witnessed and/or reported to governing authorities and the public.

To the extent not already defined, catastrophic injuries definitions are defined, for example, in the Federal system. A legal workers compensation panel including plaintiff and defense counsel is assembled locally for dispute resolution when necessary. Also, an anonymous injury fraud system is advertised and provides rewards for exposing employees who abuse the compensation system.

Demographics and statistics on extensive or top work related injuries for each job or work site, for example, each Federal installation, is gathered. Data is tabulated for the injuries that cause the extensive lost time from work and overall cost per federal installation. This data is compared with data obtained from the Bureau of Labor and Statistics for trends based on occupations and injury patterns. Diagnoses for work related musculoskeletal injuries is joint specific and provided by a specialist physician not based on the initial diagnosis by a primary care or general physician.

Embodiments of the present invention seek to create a win-win situation for all involved, improve medical outcomes, reduce the amount of loss time from work, and reduce the overall cost, for instance, to the federal government and tax payers.

These and other features and advantages will be apparent from a reading of the following detailed description and a review of the associated drawings. It is to be understood that both the foregoing general description and the following detailed description are explanatory only and are not restrictive of the invention as claimed.

DETAILED DESCRIPTION

As briefly described above, embodiments of the present invention assess and manage work-related injuries, for instance musculoskeletal injuries. In the following detailed description, references are made to the accompanying drawings that form a part hereof, and in which are shown by way of illustrations specific embodiments or examples. These embodiments may be combined, other embodiments may be utilized, and structural changes may be made without departing from the spirit or scope of the present invention. The following detailed description is therefore not to be taken in a limiting sense, and the scope of the present invention is defined by the appended claims and their equivalents.

Embodiments of the present invention advocate an active occupational orthopedic approach to injury assessment and management of work-related musculoskeletal disorders. Each patient is different in respect to their response to pain and injury. Communication with employees, employers, case managers and nurses is essential. Documentation of date of injury (DOI), work status, and treatment recommendations are invaluable. The sooner the injury rehabilitation begins the better the outcome. Local comprehensive injury management centers are provided. This process is a combined effort with civilian and Federal personnel to achieve optimal outcomes. Physicians pursued to serve on a management team provide information in a timely manner, are able to utilize a multidisciplinary approach to treatment if necessary, and have taken time to understand the workers compensation process.

Efficient evaluation and management of work-related musculoskeletal injuries, injury prevention, and rehabilitation are the main focus of treatment. If a patient is improving with conservative treatment, the physician continues with treatment goals. When the patient is not improving with non operative treatment, a surgical referral is made if surgery is necessary.

Reasonable return to work dates and modified duty goals are also developed. And regular communication with employer case management is maintained. When an injury is considered catastrophic, catastrophic case controls are initiated. Once injured worker has reached maximum medical improvement (MMI), the injury status is reviewed to determine if function capacity evaluations (FCE) are needed. Impairment ratings are assigned, a determination is made whether permanent job modifications are necessary, and vocational assessments are incorporated.

Figure 1:
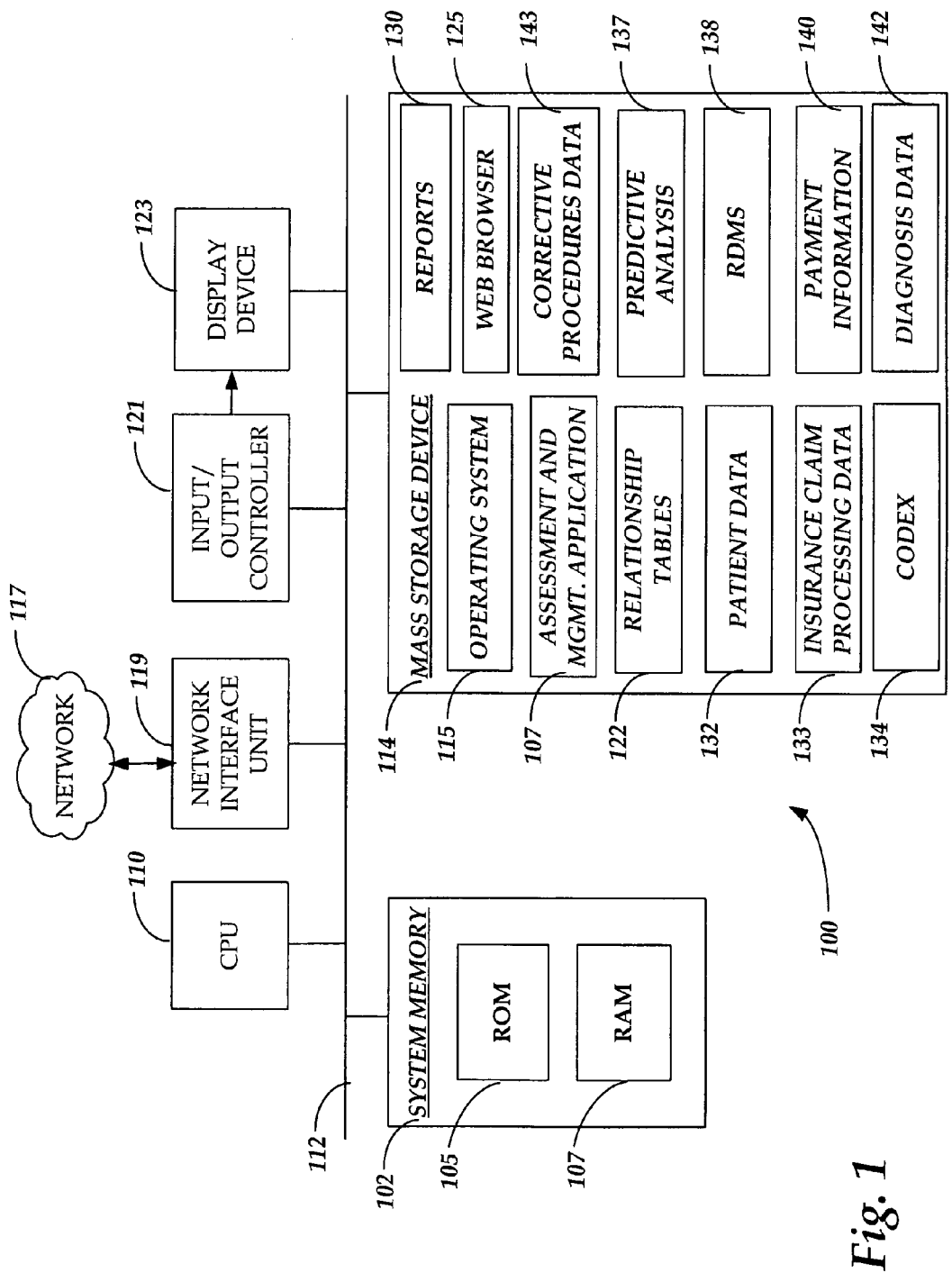
FIG. 1 illustrates computing system architecture for a computing apparatus.

Referring now to the drawings, in which like numerals refer to like elements through the several figures, aspects of the present invention and an exemplary computing operating environment will be described. FIG. 1 and the following discussion are intended to provide a brief, general description of a suitable computing environment in which the invention may be implemented. While the invention will be described in the general context of program modules that execute in conjunction with an application program that runs on an operating system on a personal or server computer, those skilled in the art will recognize that the invention may also be implemented in combination with other program modules.

Generally, program modules include routines, programs, components, data structures, and other types of structures that perform particular tasks or implement particular abstract data types. Moreover, those skilled in the art will appreciate that the invention may be practiced with other computer system configurations, including hand-held devices, multiprocessor systems, microprocessor-based or programmable consumer electronics, minicomputers, mainframe computers, and the like. The invention may also be practiced in distributed computing environments where tasks are performed by remote processing devices that are linked through a communications network. In a distributed computing environment, program modules may be located in both local and remote memory storage devices.

Embodiments of the invention may be implemented as a computer process (method), a computing system, or as an article of manufacture, such as a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process.

FIG. 1 illustrates computing system architecture for a computing apparatus 100. In a basic configuration, the computing apparatus 100 typically includes at least one processing unit 110, system memory 102, and a mass storage device (MSD) 114. Depending on the exact configuration and type of computing apparatus 102, the system memory 102 may be volatile (such as RAM 107), non-volatile (such as ROM 105, flash memory, etc.) or some combination of the two. The MSD 114 typically includes an operating system 115 suitable for controlling the operation of a networked personal or server computer, such as the WINDOWS® operating systems from MICROSOFT CORPORATION of Redmond, Wash. The MSD 114 may also include one or more software applications such as the assessment and management application 108 and a web browser 125 such as INTERNET EXPLORER from MICROSOFT CORPORATION.

The MSD 114 also includes relationship tables 122 for storing relationships drawn between injury categories, corrective procedures data 143, a predictive analysis 137 for use in generating reports 130 and making recommendations regarding assessing and managing work-related injuries. Still further, the MSD 114 may include patient data 132, a relational database management system (RDMS) 138, insurance claim processing data (ICPD) 133, payment information 140, an industry validated database for ICD codes, such as CODEX 134, and diagnosis data 142. It should be appreciated that one or more of the preceding data and program modules may also reside on the memory of remote computers and interface with the computing apparatus 100 via the network 117.

The MSD 114 is connected to the CPU 110 through a mass storage controller (not shown) connected to the system bus 112. The MSD 114 and its associated computer-readable media, provide non-volatile storage for the computing apparatus 100. Although the description of computer-readable media contained herein refers to a MSD, such as a hard disk or RAID array, it should be appreciated by those skilled in the art that computer-readable media can be any available media that can be accessed by the CPU 110.

The CPU 110 may store data to and access data from the MSD 114. Data is transferred to and received from the MSD 114 through the system bus 112. The CPU 110 may be a general-purpose computer processor. Furthermore, as mentioned below, the CPU 110, in addition to being a general-purpose programmable processor, may be firmware, hard-wired logic, analog circuitry, other special purpose circuitry, or any combination thereof.

According to various embodiments of the invention, the computing apparatus 100 can operate in a networked environment, using logical connections to remote computing devices via network communication, such as an Intranet, or a local area network (LAN) or wide area network (WAN). The computing apparatus 100 may connect to a network 117 via a network interface unit 119. It should be appreciated that the network interface unit 119 may also be utilized to connect to other types of networks and remote computer systems. The computing apparatus 100 also includes an input/output controller 121 for receiving and processing input from a number of devices, including a keyboard (not shown). Similarly, the input/output controller 121 provides output to a display screen 123, a printer, or other type of output device.

A computing apparatus, such as the computing apparatus 100, typically includes at least some form of computer-readable media. Computer readable media can be any available media that can be accessed by the computing apparatus 100. By way of example, and not limitation, computer-readable media might comprise computer storage media and communication media.

Computer storage media includes volatile and nonvolatile, removable and non-removable media implemented in any method or technology for storage of information such as computer readable instructions, data structures, program modules or other data. Computer storage media includes, but is not limited to, RAM, disk drives, a collection of disk drives, flash memory, other memory technology or any other medium that can be used to store the desired information and that can be accessed by the computing apparatus 100.

Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared, and other wireless media. Combinations of any of the above should also be included within the scope of computer-readable media. Computer-readable media may also be referred to as computer program product.

Figure 2:
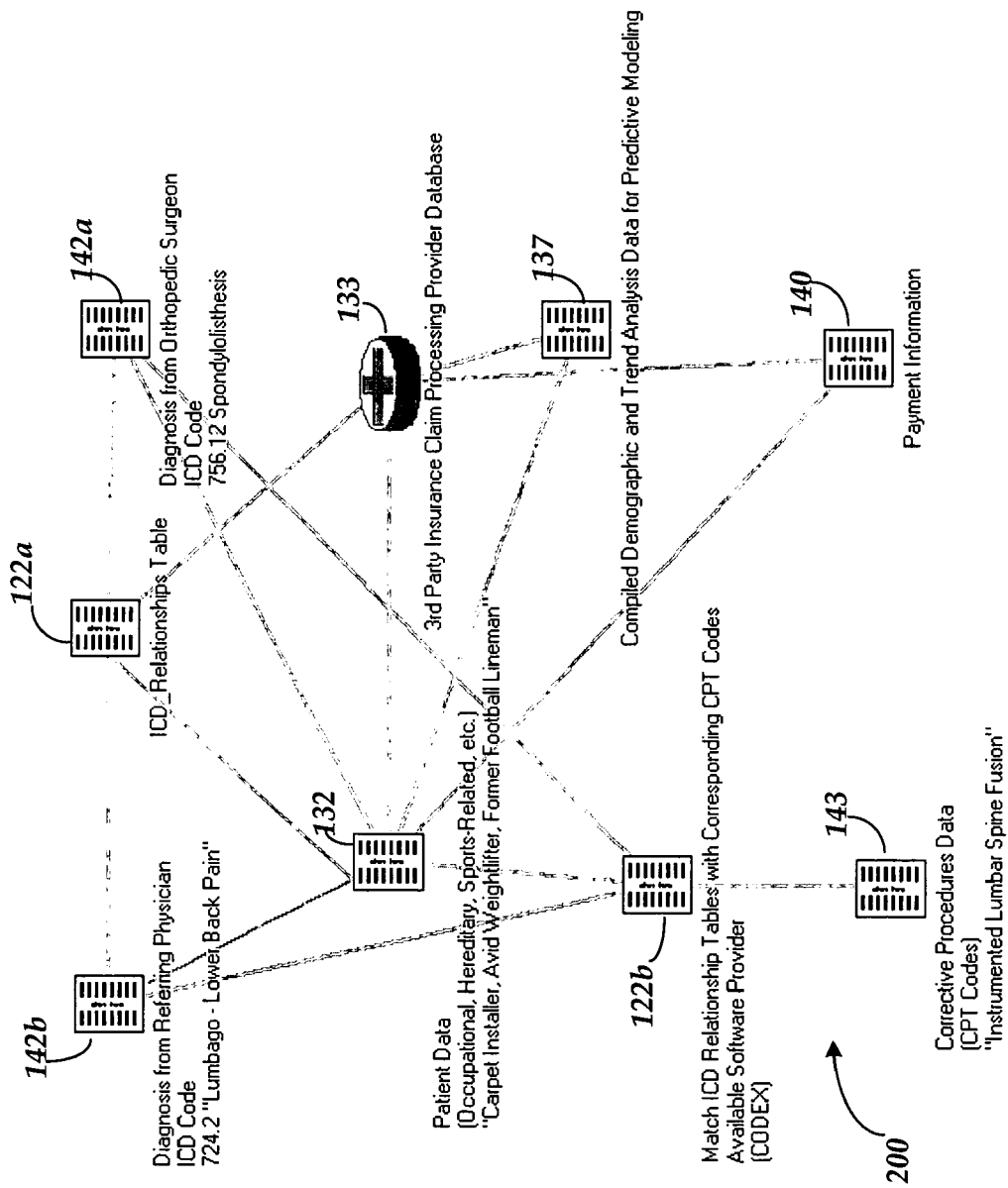
FIG. 2 illustrates how a relationship table computational component drives data analysis by creating connections between collections of medical data.

FIG. 2 illustrates how a relationship table computational component 200 drives data analysis by creating connections between collections of medical data. Conventional physicians use a periodically updated international coding database for defining patient diagnoses before treatment. The ICD coding standard (currently ICD9) provides a numeric code and a brief text description of the medical problem a physician identifies in each patient. Each ICD code is a three digit numeric value with up to two decimal places. The first character may be alphabetical. The inclusion of decimal values generally defines an increasing level of specificity. The following outline shows the basic organizational structure:

I. Ranges of base (non-decimal) numbers represent classes within the data collection. For instance codes with a base in the range of 710-739 represent "Diseases of the Musculoskeletal System and Connective Tissue". The numeric size of class ranges varies.
    A) ICD base values represent categories within the parent class. For instance 719 represent "Other and unspecified disorders of joint".
      1) The inclusion of one or two decimal values with a base value facilitates increasing levels of specificity within the diagnosis hierarchy. For instance 719.4 represents "Pain in joint" and 719.41 represents "Pain in joint (shoulder)".

The ICD coding standard provides a vehicle for somewhat consistent application of diagnosis values. However, its organization structure is insufficient for preventing informational disconnects between even slightly disparate diagnoses between physicians who evaluate the same patient for a malady and for facilitating computational linkage between specific diagnosis values and more generalized diagnosis values. The following scenario defines a typical problem with the ICD data organization:

ICD Code 719.41 represents "Pain in joint (shoulder)". ICD Code 840.4 represents "Rotator cuff sprain/strain (traumatic)". The referring physician uses 719.41 for his diagnosis, the orthopedic surgeon to whom the patient was referred uses code 840.4.

This scenario shows a typical informational disconnect caused by the structure of the ICD9 data collection. No relational construct exists within ICD to connect these two codes even though the patient's shoulder pain may be caused by a rotator cuff strain. In diagnosis scenarios where the final (specialist's) diagnosis 142*a* text is highly technical, and the referring physician's diagnosis 142*b* is generalized, it becomes increasingly difficult for a non-specialist to draw relationships between the respective ICD codes. The ability to draw relationships computationally facilitates faster resolution of insurance claims and more importantly, it provides a valuable mechanism for predictive data analysis within patient populations, which could prove a vital tool for preventative treatment.

At its core the engine for this patent's computational component is the application of specialized medical knowledge in evaluating the ICD data collection. This knowledge is systematically applied with each new release of ICD data with the primary intent of drawing relationships between ICD codes. The integrity of the defined relationships utilized within the computational component 200 may be high because the relationships are defined by licensed physicians (specialists). Therefore, in building the computational component 200, experts in the art of computer programming work directly with medical doctors in defining the ICD relationships, structuring their storage in the RDBMS 138 and developing computer programs, such as the assessment and management application 108, that utilize the relationships in compiling and retrieving valuable information.

According to an embodiment of the present invention, the computational component 200 first requires that the types of relationships defined between ICD codes be clearly delineated. Some relationships are inherent to an ICD numbering scheme. The computational component 200 is not limited to drawing relationships that are outside an inherent structure of the ICD data. The computational component 200 utilizes the inherent relationships in concordance with the novel relationships described above. Below is a list of the various relationships that may exist between two ICD codes outside the inherent ICD structure:

1) Parent-Child—one code (parent) represents a more general condition that may be caused or partially caused by a more specifically defined code (child). A child may or may not be a subcategory of the parent. For instance 719.41 "Pain in joint (shoulder)" may be a parent of 727.61 Rotator Cuff Rupture. The code 727.61 Rotator Cuff Rupture represents a more specific diagnosis than "Pain in joint (shoulder)"; however, neither is clearly a subcategory of the other.

2) Sibling-Sibling—both codes represent an equal level of specificity and may be related either as commonly coupled symptoms or as commonly confused diagnoses. For example 726.10 "Rotator cuff syndrome/tendonitis" might be a sibling of 840.4 "Rotator cuff sprain/strain (traumatic)" because their symptoms are similar.

3) Relative/Distant Relative—Any significant relationship drawn between diagnoses that does not fit the prior two categories. A system of gauging or weighting the significance of these peripheral relationships might be developed.

4) No Relation—No practical relationship drawn.

After these relationships have been defined by medical doctors working in tandem with experts in the art of computer programming, a table structure is developed within the RDBMS 138 that stores the relationships 122 and provides a foundation for relational logic using STRUCTURED QUERY LANGUAGE (SQL) from MICROSOFT Corporation of Redmond, Wash.

The following table structure facilitates linkage between ICD codes. According to an embodiment of the present invention, the table structure's basic manifestation is designed as follows. Some column names provide the meaning of the data contained within them. For others a description is provided:

| | |
|---|---|
| Table Name: | ICD_Relationships 122a |
| Column1: | ICD_Code |
| Column2: | Related_Code |
| | (Related ICD code.) |
| Column3: | Relationship |
| | (Code that defines relationship: parent-child, etc.) |
| Primary Key: | ICD_Code, Related_Code |

Databases within which the ICD Relationships table 122a is utilized contain equivalent data to the below sample tables:

| | |
|---|---|
| Table Name: | ICD_Codes |
| Table Definition: | A complete list of currently valid ICD codes. |
| Column1: | ICD_Code |
| Column2: | ICD_Description |
| Primary Key: | ICD_Code |

| | |
|---|---|
| Table Name: | Patient_Treatment |
| Table Definition: | A list of information defining diagnoses and transcription data documenting a doctor-patient interaction as related to a specific need for treatment services. |
| Column1: | Treatment_Visit_ID |
| | (Unique value representing a treatment instance between doctor and patient.) |
| Column2: | Doctor_ID |
| | (Unique value representing a physician.) |
| Column3: | Patient_ID |
| | (Unique value representing a patient.) |
| Column4: | Date_Time |
| Column5: | Transcription_Text |
| | (Text describing doctor's impressions and analysis.) |
| Primary Key: | Treatment_Visit_ID |

| | |
|---|---|
| Table Name: | Treatment_Diagnoses |
| Table Definition: | A list of information defining diagnoses and transcription data documenting a doctor-patient interaction as related to a specific need for treatment services. |
| Column1: | Treatment_Visit_ID |
| Column2: | Treatment_Visit_ICD_Code |
| | (Each visit may require multiple diagnoses and, therefore, multiple ICD codes.) |
| Column3: | Diagnosis_Rank |
| | (Each diagnosis may be optionally weighted in significance to the current treatment instance.) |
| Primary Key: | Treatment_Visit_ID, Treatment_Visit_ICD_Code |

| | |
|---|---|
| Table Name: | Patient_Data |
| Table Definition: | A list of information about a patient. A minimum quantity of information has been provided for demonstration purposes. |
| Column1: | Patient_ID |
| Column2: | Age |
| Column3: | Occupation |
| Primary Key: | Patient_ID |

SQL analysis may be applied to the sample tables in order to obtain a list of ICD child values associated with the parent of ICD value 719.41 "Pain in joint (shoulder)". The following SQL program is executed to generate the list of ICD child values:

```
select ir1.Related_Code
from ICD_Codes icd1
join ICD_Relationships ir1
    on icd1.ICD_Code = ir1.ICD_Code
join ICD_Codes icd2
    on ir1.Related_Code = icd2.ICD_Code
where ir1.ICD_Code = '719.41' and
    ir1.Relationship = 'parent-child'
```

Obtaining proportional analysis of treatment instance data is executed in a similar manner. The following program obtains a subtotaled report of child ICD values associated with the parent ICD value 719.41 "Pain in joint (shoulder)", sorted in a descending list according to frequency:

```
select ir1.Related_Code,
    total_instances = count(*)
from ICD_Codes icd1
join ICD_Relationships ir1
    on icd1.ICD_Code = ir1.ICD_Code
join ICD_Codes icd2
    on ir1.Related_Code = icd2.ICD_Code
join Treatment_Diagnoses td1
    on icd2.ICD_Code = td1.Treatment_Visit_ICD_Code
where ir1.ICD_Code = '719.41' and
    ir1.Relationship = 'parent-child'
group by ir1.Related_Code
order by count(*) descending
```

To obtain the same report filtering the data for patients who are barbers over the age of 35, the following program is executed according to an illustrative embodiment of the present invention:

```
select ir1.Related_Code,
    total_instances = count(*)
from ICD_Codes icd1
join ICD_Relationships ir1
    on icd1.ICD_Code = ir1.ICD_Code
join ICD_Codes icd2
    on ir1.Related_Code = icd2.ICD_Code
join Treatment_Diagnoses td1
    on icd2.ICD_Code = td1.Treatment_Visit_ICD_Code
join Patient_Treatment pt1
    on td1.Treatment_Visit_ID = pt1.Treatment_Visit_ID
join Patient_Data pd1
    on pt1.Patient_ID = pd1.Patient_ID
where ir1.ICD_Code = '719.41' and
    ir1.Relationship = 'parent-child' and
    pd1.Occupation = 'barber' and
    pd1.Age > 35
group by ir1.Related_Code
order by count(*) descending
```

Using the ICD Relationships table 122a, relationships are drawn between disparate physician diagnoses as well as specific patient diagnosis-treatment event time lines. This table pulls together an entire comprehensive collection of patient information, providing a previously missing linkage that reveals trends and fluctuations within the data. The ICD Relationships table 122a is joined to a doctor-patient diagnosis history table 132 and simultaneously to a patient corrective procedures table 122b and simultaneously to patient demographic, statistical or occupational activity data 137. As these three collections of data are drawn together, complex relational analysis is executed to discover trends within groups of related diagnosis codes. The computational component 200 chart illustrates how the relationship table 122a drives data analysis.

This diagram illustrates how the computational component 200 according to an embodiment of the present invention, creates connections between collections of medical data. These connections facilitate analysis at each stage of a patient's treatment. During analysis diagnosis groupings emerge, revealing frequent areas of misdiagnosis by referring physicians, generalized diagnosis code groupings from referring physicians that lead to specific diagnosis value groupings upon subsequent meetings with specialists. Corrective procedures that may be fully or partially predicted by initial diagnosis groupings for patients with specific demographic, occupational, hereditary or sports activity backgrounds are also revealed. Third party insurance claim processing providers can utilize this information to resolve issues between disparate diagnoses, and insurance companies can utilize this data to augment actuarial data.

According to an embodiment of the present invention, when the entire body of data is linked to payment information 140, diagnoses are applied strategically to maximize or minimize payment totals for treatment cycles. Diagnosis groupings created by the ICD Relationships table 122a reveal flexible diagnosis situations for patients with specific health, background and diagnosis competitions. Some ICD codes may differ from other ICD codes slightly and the accuracy of both codes as related to a specific patient situation may be fundamentally equal. However, insurance payment may differ significantly for the same treatment cycle depending on which ICD codes are chosen.

According to an embodiment of the present invention, the computational component 200 involves a relational construct that provides a previously missing link between ICD data. This link provides multifarious practical applications.

The following is a typical data storage scenario:
Codex value: Back Pain
Parent Category: Spinal Injury
Child Category: Lumbar Herniated Disk
Specific Diagnosis: L5-S1 Lateral Herniation
Specific Corrective Procedure: Microdiscectomy
Patient Data: Caucasian, Male, 37, Occupation—carpet installer, Height—5'7", Weight 255
The family physician diagnosis may have been "Back Pain", which is a parent category underneath the Codex value of "Back Pain". The linkage is easily made between all physician back pain diagnoses and CPT.

Figure 3:
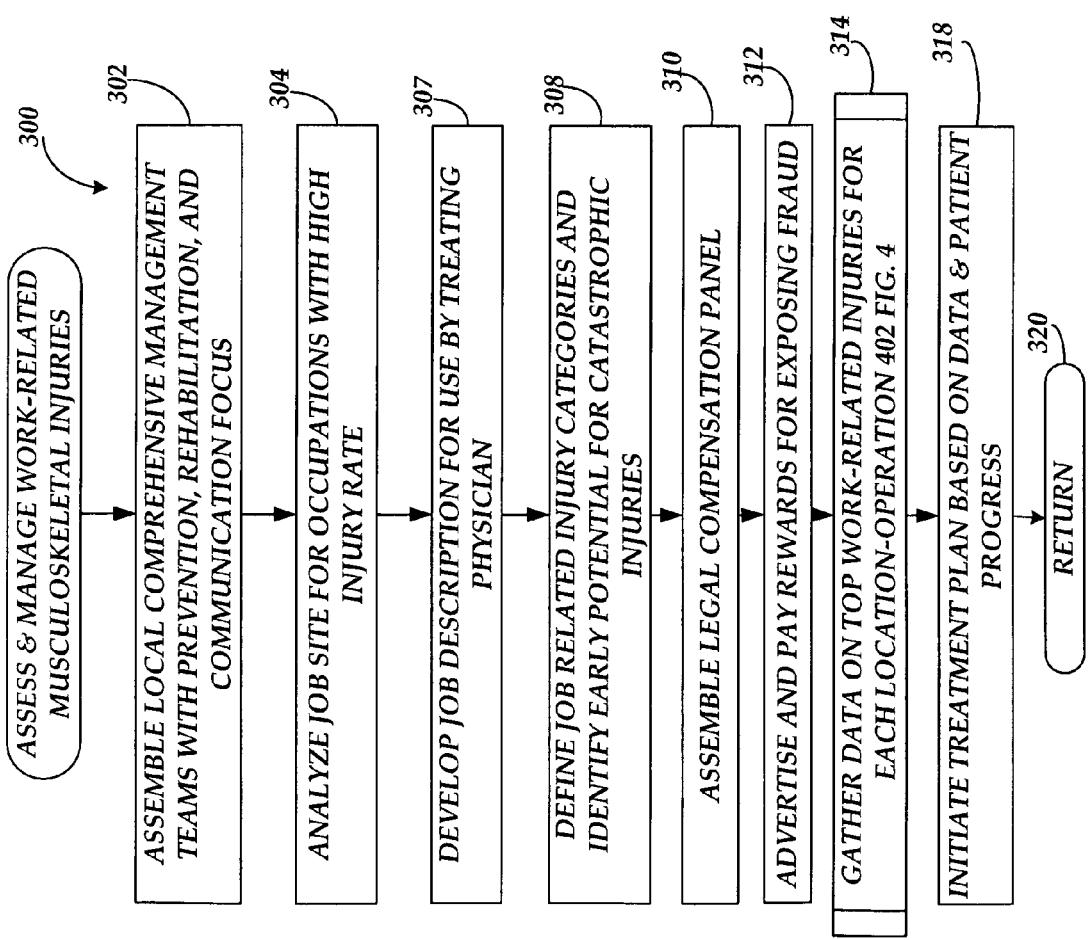
FIGS. 3-4 illustrate logical or operational flows performed in assessing and managing work-related injuries.
Figure 4:
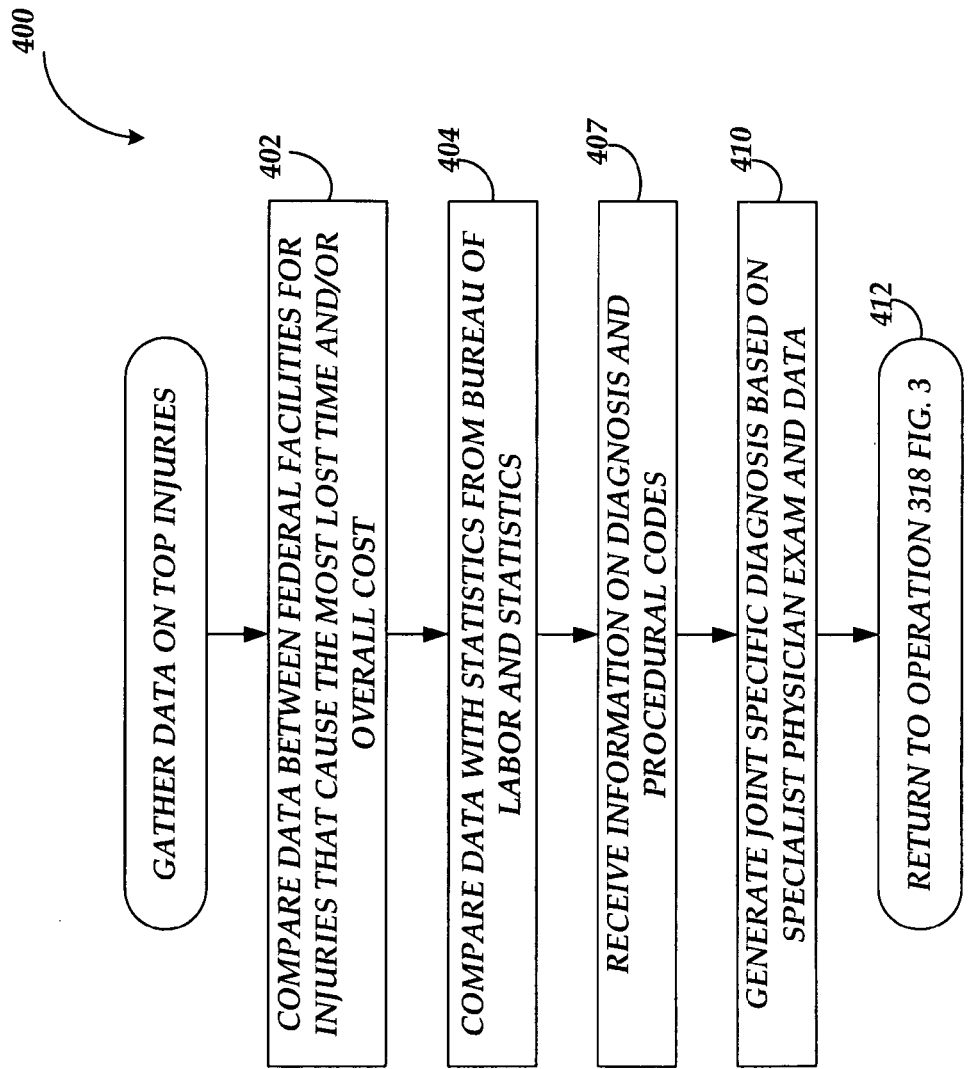

FIGS. 3-4 illustrate logical or operational flows performed in assessing and managing work-related injuries according to an embodiment of the present invention. When reading the discussion of the routines presented herein, it should be appreciated that the logical operations of various embodiments of the present invention are implemented (1) as a sequence of computer implemented acts or program modules running on a computing system and/or (2) as interconnected machine logic circuits or circuit modules within the computing system. The implementation is a matter of choice dependent on the performance requirements of the computing system implementing the invention. Accordingly, the logical operations illustrated in FIGS. 3-4, and making up the embodiments of the present invention described herein are referred to variously as operations, structural devices, acts or modules. It will be recognized by one skilled in the art that these operations, structural devices, acts and modules may be implemented in software, in firmware, in special purpose digital logic, and any combination thereof without deviating from the spirit and scope of the present invention as recited within the claims set forth herein.

Referring now to FIGS. 1-4, the operational flow 300 begins at operation 302, where a comprehensive management team having a prevention, rehabilitation, and communication focus is assembled. Key management team members include industry focused orthopedists, nurse case managers, workers compensation coordinators, a marketing staff, a clinic manager, and a physical and occupational therapist. Conservative treatment plans are initiated by a physician to include part-time (PT)/overtime (OT) evaluations, modified duty assignments, communication, and case management.

At operation 304, the computing apparatus 100 analyzes job site for occupations with high injury profiles or rates, for instance, occupations with excessive injury lost work time or medical cost.

Next, at operation 307, the computing apparatus 100 develops a job description of the occupation in question for use by the treating physician. This job description will provide the treating physician with insight into a patient's workload and/or necessary modifications.

At operation 308, the computing apparatus 100 defines job-related injury categories and identifies early potential for catastrophic injuries. The logical flow 300 then continues to operation 310 where a legal compensation panel is assembled. The legal panel's responsibilities include: assuring federal compensation regulations are followed by employer and employees, overseeing surveillance of patients who may be defrauding the government by faking injuries, insuring proper settlements for case closure, coordinating care by the medical team, and mediating legal matters for employer-employee disputes.

At operation 312, payments of rewards for exposing injury fraud are advertised. This is likely to deter fraudulent activity. Then at operation 314, the computing apparatus 100 gathers demographics and statistics associated with the top work-related injuries at each work site. Additional details regarding gathering demographics and statistics associated with the top injuries are described below with respect to FIG. 4.

Next at operation 318, the computing apparatus 100 initiates a treatment plan based on gathered data and patient progress. The operational flow 300 returns control to other routines at return operation.

Referring to FIG. 4, operational flow 400 begins at operation 402 where, the computing apparatus 100 compares, between Federal installations or facilities, injury data for injuries associated with excessive loss work time and/or medical cost. Next at operation 404, the computing apparatus 100 compares injury data with statistics from the Bureau for Labor and Statistics. This comparison helps to determine effective relationships to help in assessing and managing the injury.

At operation 407, the computing apparatus 100 receives diagnosis and current procedural codes associated with certain injuries. Then at operation 410, the computing apparatus 100 generates joint specific diagnosis for the work-related injury based on a specialist physician's exam and relationship data. The operational flow 400 returns control to operation 318 at return operation 412.

Thus, the present invention is presently embodied as methods, systems, computer program products or computer readable mediums encoding computer programs for assessing and managing work-related musculoskeletal injuries.

It will be apparent to those skilled in the art that various modifications or variations may be made in the present invention without departing from the scope or spirit of the invention. Other embodiments of the present invention will be apparent to those skilled in the art from consideration of the specification and practice of the invention disclosed herein.

What is claimed is:

1. A method for assessing and managing a work-related musculoskeletal injury associated with at least one work site with a non-transitory computer-readable medium, the method comprising:
receiving musculoskeletal injury categories;
drawing, by a computer, relationships between the musculoskeletal injury categories by applying specialized medical knowledge, wherein the relationships between the musculoskeletal injury categories and the current procedural terminology comprises drawing relationships between specific procedural terminology and generalized procedural terminology, the relationships being determined, at least in part, by analyzing the table structure to determined trends, the trends being indicative of the relationships between the musculoskeletal injury categories and the current procedural terminology;
structuring storage of the relationships between the musculoskeletal injury categories by tabulating a table structure that facilitates computational linkage between specific musculoskeletal injury categories and generalized musculoskeletal injury categories, wherein tabulating the table structure comprises joining, to the table structure, at least one of the following: a doctor-patient diagnosis history table, a patient corrective procedures table, demographic data, statistical data, and occupational data;
gathering, for each work site, statistics on work-related musculoskeletal injuries associated with at least one of the following: relatively high lost work time and relatively high medical cost; and
utilizing the relationships and the statistics to compile and retrieve data that facilitates improved work-related musculoskeletal injury resolution, wherein the improved work-related musculoskeletal injury resolution comprises at least one of the following:
effective treatment of the work-related musculoskeletal injury;
faster resolution and payment of an insurance claim associated with the work-related musculoskeletal injury;
reduction in lost work time associated with the work-related musculoskeletal injury; and
reduction in medical cost associated with the work-related musculoskeletal injury.

2. The method of claim 1, further comprising utilizing the relationships and the statistics to compile and retrieve data that facilitates improved work-related musculoskeletal injury resolution wherein the improved work-related musculoskeletal injury resolution comprises at least one of the following:
effective treatment of the work-related musculoskeletal injury;
faster resolution and payment of an insurance claim associated with the work-related musculoskeletal injury;
reduction in lost work time associated with the work-related musculoskeletal injury; and
reduction in medical cost associated with the work-related musculoskeletal injury.

3. The method of claim 2, further comprising initiating a treatment plan based on the data that facilitates the improved work-related musculoskeletal injury resolution and progress of the patient.

4. The method of claim 2, wherein structuring storage of the relationships comprises tabulating a table structure that facilitates computational linkage between specific and generalized musculoskeletal injury categories.

5. The method of claim 4, further comprising prior to drawing the relationships, assembling a management team associated with the at least one work site wherein the management team comprises a physician specializing in musculoskeletal injuries and at least one of the following:
- a nurse case manager;
- a compensation coordinators;
- a marketing staff;
- a physical therapist;
- an occupational therapist; and
- a vocational rehabilitation specialist.

6. The method of claim 1, further comprising:
- analyzing the work site for occupations having a high injury profile;
- developing a job description associated with each occupation having the high injury profile for use by a physician treating the work-related musculoskeletal injury;
- identifying potential catastrophic work-related injuries based on the job description and analyzing the work site; and
- implementing early intervention measures to prevent the potential catastrophic injuries.

7. The method of claim 1, further comprising:
- assembling a legal panel to resolve disputes regarding injury compensation; and
- advertising and paying rewards for anonymously exposing injury fraud.

8. The method of claim 1, wherein gathering the statistics comprises:
- comparing data between work sites related to the work-related musculoskeletal injuries associated with at least one of the following: relatively high lost time and relatively high medical cost;
- comparing the data between work sites with statistics from a bureau of labor and statistics associated with the work-related musculoskeletal injury;
- receiving diagnosis and procedural codes associated with the musculoskeletal injury categories; and
- receiving a joint specific diagnosis based on an exam of the patient by a physician specializing in musculoskeletal injuries.

9. The method of claim 1, wherein defining musculoskeletal injury categories comprises agreeing upon the categories between every agency involved in resolving the work-related musculoskeletal injury.

10. The method of claim 1, wherein drawing relationships between the musculoskeletal injury categories comprises delineating a type of relationships between international classification of disease (ICD) codes wherein the type of relationship comprises at least one of the following:
- a parent-child relationship wherein one parent ICD code represents a general condition that can be caused by a more specific condition represented by a child ICD code;
- a sibling-sibling relationship wherein at least two ICD codes represent conditions of an equal level of specificity and are related as one of the following: commonly coupled symptoms and commonly confused diagnoses; and
- a relative-distant relative relationship comprising a relationship drawn between diagnoses that does not fit one of the following: the parent-child and the sibling-sibling relationship.

11. A computer program product comprising a non-transitory computer-readable medium having control logic stored therein for causing a computer to assess and manage a work-related musculoskeletal injury associated with at least one work site, the control logic comprising computer-readable program code for causing the computer to:
- receive musculoskeletal injury categories;
- structure storage of relationships between the musculoskeletal injury categories by tabulating a table structure that facilitates computational linkage between specific musculoskeletal injury categories and generalized musculoskeletal injury categories, wherein tabulating the table structure comprises joining, to the table structure, at least one of the following: a doctor-patient diagnosis history table, a patient corrective procedures table, demographic data, statistical data, and occupational data;
- draw relationships between the musculoskeletal injury categories and current procedural terminology by applying specialized medical knowledge, wherein the relationships between the musculoskeletal injury categories and the current procedural terminology comprises drawing relationships between specific procedural terminology and generalized procedural terminology, the relationships being determined, at least in part, by analyzing the table structure to determine trends, the trends being indicative of the relationships between the musculoskeletal injury categories and the current procedural terminology;
- gather for each work site, statistics on work-related musculoskeletal injuries associated with a relatively high frequency; and
- utilize the relationships and the statistics to compile and retrieve data that facilitates improved work-related musculoskeletal injury resolution wherein improved work-related musculoskeletal injury resolution comprises at least one of the following:
  - effective treatment of the work-related musculoskeletal injury;
  - faster resolution and payment of an insurance claim associated with the work-related musculoskeletal injury;
  - reduction in lost work time associated with the work-related musculoskeletal injury; and
  - reduction in medical cost associated with the work-related musculoskeletal injury.

12. The computer program product of claim 11, wherein computer-readable program code for causing the computer to structure storage of the relationships comprises computer-readable program code for causing the computer to tabulate the table structure that facilitates computational linkage between the specific procedural terminology and the generalized procedural terminology.

13. The computer program product of claim 12, further comprising computer-readable program code for causing the computer to initiate a treatment plan based on data that facilitates improved work-related musculoskeletal injury resolution and progress of the patient.

14. The computer program product of claim 11, wherein the computer-readable program code for causing the computer to gather the statistics comprises computer-readable program code for causing the computer to:
- compare data between work sites related to the work-related musculoskeletal injuries associated with relatively high injury rates;
- compare the data between work sites with statistics from a bureau of labor and statistics associated with the work-related musculoskeletal injury;
- receive diagnosis and procedural codes associated with the musculoskeletal injury categories; and receive a joint specific diagnosis based on an exam of the patient by a physician specializing in musculoskeletal injuries.

15. The computer program product of claim 11, wherein the computer-readable program code for causing the computer to draw relationships between the musculoskeletal injury categories comprises computer-readable program code for causing the computer to delineate a type of relationships between international classification of disease (ICD) codes wherein the type of relationship comprises at least one of the following:
- a parent-child relationship wherein one parent ICD code represents a general condition that can be caused by a more specific condition represented by a child ICD code;
- a sibling-sibling relationship wherein at least two ICD codes represent conditions of an equal level of specificity and are related one of the following: commonly coupled symptoms and commonly confused diagnoses; and
- a relative-distant relative relationship comprising a relationship drawn between diagnoses that does not fit one of the following: the parent-child and the sibling-sibling relationship.

16. A method for assessing job-related musculoskeletal injuries with a non-transitory computer-readable medium, the method comprising:
- receiving musculoskeletal injury categories;
- drawing, by a computer, relationships between the musculoskeletal injury categories and current procedural terminology by applying specialized medical knowledge, wherein the relationships between the musculoskeletal injury categories and the current procedural terminology comprises drawing relationships between specific procedural terminology and generalized procedural terminology, the relationships being determined, at least in part, by analyzing the table structure to determined trends, the trends being indicative of the relationships between the musculoskeletal injury categories and the current procedural terminology;
- structuring storage of the relationships between the musculoskeletal injury categories by tabulating a table structure that facilitates computational linkage between specific musculoskeletal injury categories and generalized musculoskeletal injury categories, wherein tabulating the table structure comprises joining, to the table structure, at least one of the following: a doctor-patient diagnosis history table, a patient corrective procedures table, demographic data, statistical data, and occupational data;
- gathering statistics on job-related musculoskeletal injuries associated with at least one of the following: relatively high lost work time and relatively high medical cost; and
- utilizing the relationships and the statistics to compile data that facilitates improved work-related musculoskeletal injury resolution, wherein the improved work-related musculoskeletal injury resolution comprises at least one of the following:
  - effective treatment of the work-related musculoskeletal injury;
  - faster resolution and payment of an insurance claim associated with the work-related musculoskeletal injury;
  - reduction in lost work time associated with the work-related musculoskeletal injury; and
  - reduction in medical cost associated with the work-related musculoskeletal injury.

17. The method of claim 16, further comprising utilizing the relationships and the statistics to compile data that facilitates improved work-related musculoskeletal injury resolution wherein improved work-related musculoskeletal injury resolution comprises at least one of the following:
- effective treatment of the work-related musculoskeletal injuries;
- faster resolution and payment of insurance claims associated with the work-related musculoskeletal injury;
- reduction in lost work time associated with the work-related musculoskeletal injuries; and
- reduction in medical cost associated with the work-related musculoskeletal injuries.

18. The method of claim 17, wherein receiving musculoskeletal injury categories comprises receiving international classification of disease international classification of disease (ICD) codes.

* * * * *